United States Patent
Johnston

(10) Patent No.: US 9,641,125 B2
(45) Date of Patent: May 2, 2017

(54) LUMINESCENCE IMAGING SYSTEMS AND METHODS FOR EVALUATING PHOTOVOLTAIC DEVICES

(71) Applicant: Alliance for Sustainable Energy, LLC, Golden, CO (US)

(72) Inventor: Steven Johnston, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/002,628

(22) Filed: Jan. 21, 2016

(65) Prior Publication Data

US 2016/0218670 A1    Jul. 28, 2016

Related U.S. Application Data

(60) Provisional application No. 62/107,328, filed on Jan. 23, 2015.

(51) Int. Cl.
| | | |
|---|---|---|
| G01N 21/64 | (2006.01) | |
| H02S 50/15 | (2014.01) | |
| G01N 21/63 | (2006.01) | |
| G01N 21/956 | (2006.01) | |

(52) U.S. Cl.
CPC ............ *H02S 50/15* (2014.12); *G01N 21/63* (2013.01); *G01N 21/6489* (2013.01); *G01N 21/956* (2013.01); *G01N 2021/646* (2013.01)

(58) Field of Classification Search
CPC ................................................. G01N 21/6489
See application file for complete search history.

(56) References Cited

U.S. PATENT DOCUMENTS

| | | |
|---|---|---|
| 2011/0012636 A1 | 1/2011 | Carstensen |
| 2014/0039820 A1 | 2/2014 | Trupke et al. |
| 2016/0084764 A1* | 3/2016 | Trupke .......................... 250/206 |

FOREIGN PATENT DOCUMENTS

WO    WO 2010/130013 A1    11/2010

OTHER PUBLICATIONS

Courtois, G., et al., "Investigation of silicon heterojunction solar cells by photoluminescence under DC-bias", EPJ Photovoltaics, vol. 4, 2013, pp. 45106-1-45106-5.
DeGraaff, D., et al., "Degradation Mechanisms in Si Module Technologies Observed in the Field: Their Analysis and Statistics", NREL 2011 Photovoltaic Module Reliability Workshop, Golden, Colorado, Feb. 16, 2011, pp. 1-25.
Johnston, S., et al., "Correlations of Cu(In, Ga)Se$_2$ imaging with device performance, defects, and microstructural properties", Journal of Vacuum Science Technology A, vol. 30, No. 4, Jul./Aug. 2012, pp. 04D111-1-04D111-6.
Jordan, D., et al., "Photovoltaic Degradation Rates—An Analytical Review", NREL/JA-5200-51664, Jun. 2012, pp. 1-32.

(Continued)

*Primary Examiner* — David Porta
*Assistant Examiner* — Hugh H Maupin
(74) *Attorney, Agent, or Firm* — Michael A. McIntyre

(57) ABSTRACT

The present disclosure relates to optical methods and systems for detecting defects in photovoltaic (PV) devices such as PV cells, PV panels, PV modules, and PV arrays.

20 Claims, 15 Drawing Sheets

(56) References Cited

OTHER PUBLICATIONS

Liu, J., et al., "Non-contact Determination of Local Efficiency of mc-Si Solar Cells Using Quantitative Lock-In Thermographic and Carrierographic (Photoluminescence) Imaging", published online Nov. 7, 2014, pp. 1-10.

Ott, T., et al., "2D network simulation and luminescence characterization of Cu(ln,Ga)Se2 thin film modules", Progress in Photovoltaics: Research and Applications, vol. 20, Issue 5, Aug. 2012, pp. 600-605.

Pingel, S., et al., "Initial Degradation of Industrial Silicon Solar Cells in Solar Cells in Solar Panels", $25^{th}$ EU-PVSEC, Sep. 6-9, 2010, Valencia, Spain, 6 pages.

Shinde, K., et al., *Phosphate Phosphors for Solid-State Lighting*, Chapter 2, "Basic Mechanisms of Photoluminescence", Springer Series in Materials Science, Springer-Verlag Berlin Heidelberg 2013, pp. 41-59.

Solar Zentrum Stuttgart, "Mobile ElectroLuminescence Inspection", https://web.archive.org/web/20130402064115/http://www.solarzentrum-stuttgart.com/handouts/19_MELi_handout.pdf (Online on Apr. 2, 2013).

Solar Zentrum Stuttgart, "PV Module Electroluminescence: Enlightening Defects", http://www.uspvmc.org/proceedings/Infrared_Thermography_Workshop_0711/4.%20Daylight%20Luminescence%20(DaySy).pdf (Last modified on Jul. 25, 2013).

Sopori, B., et al., "Understanding Light-Induced Degradation of c-Si Solar Cells", presented at the 2012 IEEE Photovoltaic Specialists Conference, Jun. 3-8, 2012, Austin, Texas, pp. 1-5 (NREL/CP-5200-54200 Jun. 2012).

Stoicescu, L., et al., "Daylight Luminescence for Photovoltaic System Testing", Proceedings of the $22^{nd}$ International Photocoltaic Science and Engineering Conference, Nov. 5-9, 2012, Hangzhow, China.

Stojan, R., et al., "Luminescence radiation spectroscopy of silicon solar cells", presented at the Proceedings of the SPIE, vol. 8825, Sep. 24, 2013, pp. 88250T-1-8825-0T-6.

ARC Photovoltaics Centre of Excellence, University of NW South Wales, ARC Photovoltaics Nov. 2010 Annual Report, pp. 100-105.

Ebner et al., "Non-destructive techniques for quality control of PV modules: infrared thermography, electro- and photoluminescence imaging," IECON 2013, 39th Annual Conference of IEEE, pp. 8104-8109.

Kasemann et al., "Contactless Qualitative Series Resistance Imaging on Solar Cells," IEEE Journal of Photovoltaics, vol. 2, No. 2, Apr. 2012, pp. 181-183.

Sinton, R., "Contactless Electroluminescence For Shunt-Value Measurement in Solar Cells," 23rd European Photovoltaic Solar Energy Conference, Sep. 1-5, 2008, Valencia, Spain, pp. 1157-1159.

* cited by examiner

LUMINESCENCE IMAGING SYSTEMS AND METHODS FOR EVALUATING PHOTOVOLTAIC DEVICES

CROSS-REFERENCE TO RELATED APPLICATIONS

This application claims the benefit of U.S. Provisional Application No. 62/107,328 filed Jan. 23, 2015, the contents of which are incorporated herein by reference in their entirety.

The United States Government has rights in this invention under Contract No. DE-AC36-08GO28308 between the United States Department of Energy and the Alliance for Sustainable Energy, LLC, the Manager and Operator of the National Renewable Energy Laboratory.

BACKGROUND OF DISCLOSURE

Referring to FIG. 1, photovoltaic (PV) cells 100 are semiconductor devices that convert light into electricity. A plurality of PV cells 100 may be connected electrically in series and/or parallel circuits to produce higher voltages, currents and power levels, to produce a large-scale solar power system. For example, groups of PV cells 100 may be electrically configured into prewired units called PV modules 110 with one or more PV modules 110 assembled as a pre-wired, field-installable unit, or PV panel 120. Finally, a PV array 130 is the complete power-generating unit, including any desired number of PV panels 120. PV systems may operate in parallel with, and interconnected to, the utility grid. For example, the Agua Caliente solar power system in Arizona has approximately 5 million PV panels and generates about 290 megawatts of power, enough electricity to power about 230,000 homes at peak capacity.

Like any other manufactured device that is exposed to environmental stresses, PV devices and their performance degrade with time and possess finite lifespans. Because it has no moving parts (the major source of reliability issues in other types of electrical generating systems), a PV device's operating life is largely determined by the stability and resistance to corrosion of the materials from which it is constructed.

Thus, as PV technology becomes more efficient and economical, continued growth and investment into the PV industry requires accurate predictions of PV device degradation and degradation rates. In addition, PV array owners and operators require methods for identifying the formation of defects in their PV devices operating in the field to assist with maintenance planning and scheduling to insure that their power plants continue to perform at the plants' nameplate power capacities.

To address these needs, various groups have developed inspection methods for assessing the condition and performance of PV devices. For example, some methods have utilized electroluminescence and/or photoluminescence imaging methods. For example, the Daylight Luminescence System (DaySys) developed at the Institute of Photovoltaics at Germany's University of Stuttgart (Daylight Luminescence for Photovoltaic System Testing L. Stoicescu, M. Reuter, and J. H. Werner in *Proc. 22$^{nd}$ International Photovoltaic Science and Engineering Conference*, edited by: (Hangzhou, China, 2012), (2012)). In this example, the PV device is connected to a modulation device, and an algorithm extracts electroluminescence generated images from a video stream of the PV device. However, this method requires electrical connection of the PV device being tested to an external power source, e.g. biased voltage supply. Photoluminescence, which typically involves illuminating and imaging the same section of a PV cell, causes photoluminescence of all of the PV cell being analyzed, regardless of whether portions of the section contain disconnects (e.g. due to cracks and/or breakage).

Thus, most methods for detecting defects in PV devices today are either limited to laboratory scale testing, require expensive specialized lasers and filters, or require connecting some sort of modulating and/or bias providing device. Therefore, although progress has been made in developing methods for detecting defects in PV cells, PV modules, PV panels, and/or PV arrays in the field, there is still significant need for simpler, safer, faster, more scaleable and more reliable methods and systems that detect defects in PV devices in the field and where ever PV arrays are used.

SUMMARY OF INVENTION

An aspect of the present invention is a method that includes illuminating, using a non-solar light source, a first portion of a surface of a photovoltaic (PV) device, collecting, using a detector, a first set of measurements relating to at least one of the presence or absence of luminescence from a second portion of the surface that is not illuminated by the non-solar light source, and analyzing the first set of measurements to produce a first representation of the surface. The first representation identifies at least one of a first luminescing region or a first non-luminescing region within the second portion of the surface. The first portion of the surface and the second portion of the surface are electrically connected. In some embodiments of the present invention, the illuminating and collecting may be completed without attaching an external power source to the PV device and without detaching the PV device from a power component used during normal operation of the PV device.

In some embodiments of the present invention, the method may include stopping the illuminating of the first portion of the surface by the non-solar light source, subsequently illuminating, using the non-solar light source, the second portion of the surface, and collecting, using a detector, a second set of measurements relating to at least one of the presence or absence of luminescence from the first portion of the surface that is not illuminated by the non-solar light source. The method may include analyzing the second set of measurements to produce a second representation of the surface, wherein the second representation identifies at least one of a second luminescing region or a second non-luminescing region within the first portion of the surface, and combining the first representation with the second representation to produce a composite representation of the surface that includes both the first portion and the second portion of the surface.

In some embodiments of the present invention, the illuminating and the collecting may be performed while the surface of the PV device is further illuminated using a solar light source. The illuminating using the non-solar light source may include at least one of pulsing or modulating the non-solar light source. The non-solar light source may provide light that includes at least one wavelength of less than about 1100 nm. The non-solar light source may include at least one of a light-emitting diode (LED) light, an incandescent light, a fluorescent light, a laser diode light, and/or a halogen light.

In some embodiments of the present invention, the first set of measurements and the second set of measurements may include luminescence intensity data from the second portion and the first portion of the surface, respectively. The luminescence intensity data may be for light emitted with wavelengths greater than the at least one wavelength of the light provided by the non-solar light source.

In some embodiments of the present invention, the detector may include at least one of a silicon camera or an indium-gallium-arsenide camera. In some embodiments of the present invention, the camera may include at least one of a charge-coupled camera or a complimentary metal-oxide-semiconductor camera. The non-solar light source and the detector may be moved as a unit. The detector may be moved independently of the non-solar light source.

In some embodiments of the present invention, the illuminating and the collecting may be performed with both the non-solar light source and the detector within a distance of about six meters or less from the PV device. The illuminating and the collecting may be performed with both the non-solar light source and the detector at a distance greater than about six meters from the PV device.

An aspect of the present invention is a system that includes a non-solar light source configured to produce non-solar light having at least one wavelength less than about 1100 nm, and a camera configured to detect emitted light having a wavelength greater than the at least one wavelength produced by the non-solar light source. The non-solar light source is configured to direct the non-solar light substantially towards a first target, and the camera is configured to receive the emitted light from a second target that is electrically connected to the first target.

In some embodiments of the present invention, the non-solar light source may include at least one of a light-emitting diode (LED) light, an incandescent light, a fluorescent light, a laser diode light, and/or a halogen light. The camera may include at least one of a silicon camera or an indium-gallium-arsenide camera.

The system may include a housing, such that the non-solar light source may be positioned within the housing. The housing may include an aperture, and the non-solar light produced by the light source may pass through the aperture. The system may include a support frame, where the housing and the camera may be physically connected to the support frame, such that the housing, the non-solar light source, and the camera may move as a unit when the support frame is moved.

BRIEF DESCRIPTION OF THE DRAWINGS

Exemplary embodiments are illustrated in referenced figures of the drawings. It is intended that the embodiments and figures disclosed herein are to be considered illustrative rather than limiting.

REFERENCE NUMBERS

Figure 1:
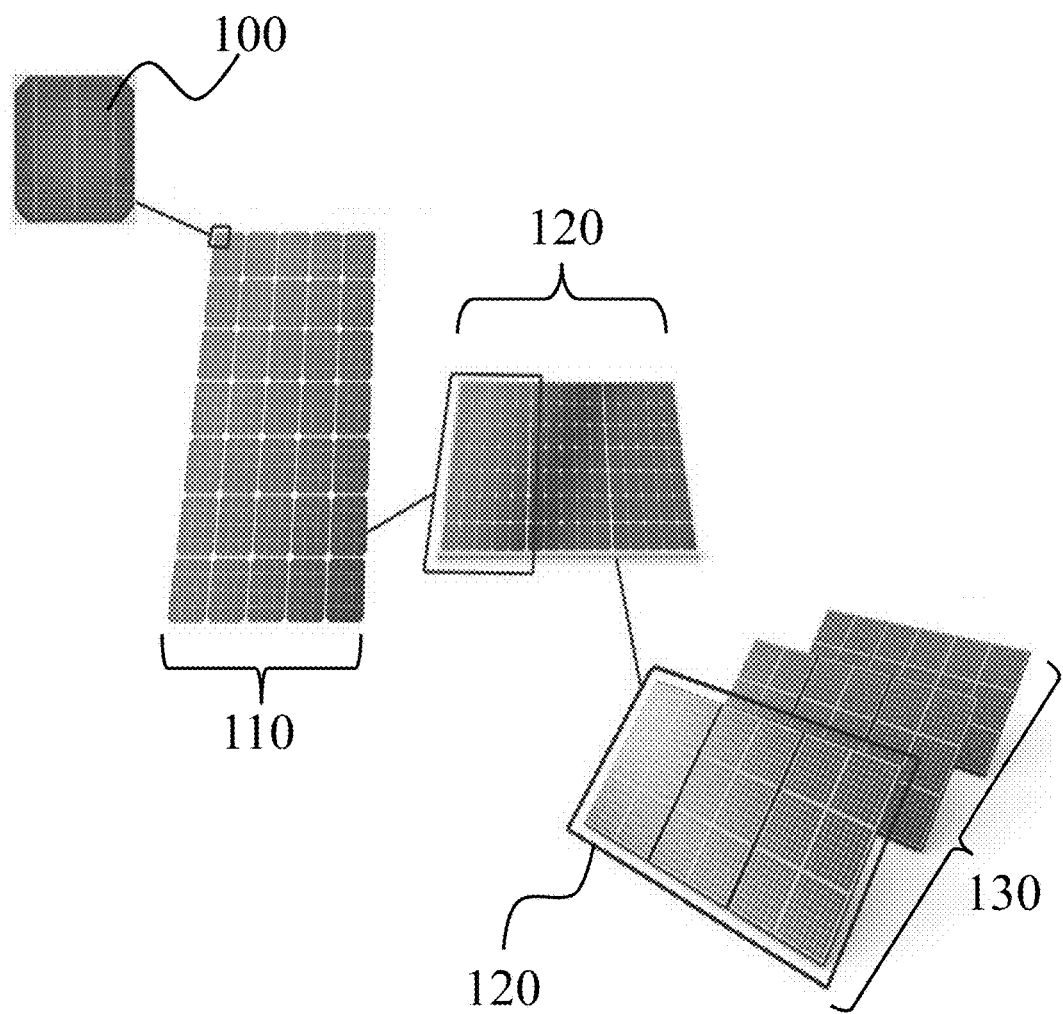
FIG. 1 illustrates the components typically used to construct a PV array for solar power systems.

100 . . . PV cell
110 . . . and 300 PV module
120 . . . PV panel
130 . . . PV array
200 . . . PV device
210 and 215 . . . illuminated portion
220 and 225 . . . non-illuminated portion
230 and 235 . . . defect (e.g. crack)
240 and 245 . . . luminescing portion
250 and 255 . . . non-luminescing portion
260 . . . composite image
270 . . . effective area
280 and 285 . . . ineffective area
310 to 380 . . . PV cells
390 to 394 . . . illuminated portion
400 to 418 . . . luminescing portion
600 . . . detection system
610 . . . support frame
620 . . . camera
630 . . . data cable
640 . . . first light source
645 . . . second light source
650 . . . power cables
660 . . . first housing
665 . . . second housing
670 . . . first aperture
675 . . . second aperture
700 . . . image

DETAILED DESCRIPTION OF EXEMPLARY EMBODIMENTS

An aspect of the present invention is a method or system for determining the presence or absence of at least one defect in a PV device in the field using a luminescence technique or method that does not require that a component of the PV device be physically manipulated or changed in order to complete the test; e.g. a component does not need to be disconnected from its normal operational circuit, nor does an additional modulated power supply need to be connected and/or any other equipment, device, or system. Thus, the PV device to be tested using the methods and systems described herein may be tested "as is" in the field, without any modifications to the PV device. This feature provides a PV device test method/system that is quicker, more efficient, less costly, and safer. As used herein, PV devices include, but are not limited to, PV cells, PV modules, PV panels, and/or PV arrays configured to receive electromagnetic radiation (e.g. solar energy) and convert that radiation to electricity.

The methods and systems described herein may detect or identify many different defects in PV devices. These include, but are not limited to, degradation of PV cells due to decreased adherence of contacts or corrosion of contacts, migration of metal through the p-n junction, short circuit failures, open circuit failures, or combinations thereof. Similarly, the methods and systems described herein may detect defects at the PV module level of the PV array, including open circuit failures, short circuit failures, delamination, cracking, electrochemical corrosion, hot-spot failures, by-pass diode failures, any other common PV module failures, and/or combinations thereof.

Thus, the methods described herein may generally be described as useful for identifying defects in PV devices. These methods include illuminating a first portion of the surface such that the illumination causes formation of a voltage within the device and the voltage induces luminescence in a second portion of the surface that is different from the first portion, and the first and second portions do not substantially overlap. The methods also include detecting the luminescence in the second portion of the surface, and from the detecting, determining the presence or absence of one or more defects in the second portion of the surface.

The methods for determining the presence or absence of defects may include processing a signal of the luminescence created by the illumination to create a one-dimensional or two-dimensional representation of the second portion of the surface. For example, a representation of the second, non-illuminated portion of the surface of the PV device may include at least one of an image, a photograph, a gray-scale image, and/or any other suitable visual representation. In other examples, the methods for determining the absence or presence of defects in a PV device may include combining at least two representations into a single composite representation.

The illuminating, detecting, and determining steps of the methods described herein may be performed without physically connecting the PV device to an additional device and/or disconnecting the PV device to an additional device; e.g. a device that provides a biased voltage and/or any other device that facilitates at least one of the illuminating, detecting, or determining. Thus, the methods described herein for detecting defects in a PV device may be successfully accomplished without disconnecting the PV device from its PV array, system, or inverter electronics, and/or without connecting the PV device to a power supply such as a voltage source. This minimizes the steps required by a technician in the field to complete an evaluation of the PV devices in question.

The PV device evaluation systems and methods may include a light source configured to illuminate a first portion of a surface of the PV device, a detector configured to detect luminescence from a second portion of the surface that is different from and does not substantially overlap the first portion, and an imaging processor that receives the detected luminescence and determines the presence or absence of defects in the second portion of the surface. The imaging processor may create a one-dimensional and/or two-dimensional representation of the second portion of the surface, where the representation may include at least one of an image, a photograph, a gray-scale image, and/or any other suitable visual representation. The illuminating may be accomplished using, for example, a light emitting diode (LED) lighting system. The detecting may be accomplished using a camera, such that the map created corresponds to a photograph.

The methods for detecting defects in a PV device described herein may optically (e.g. using a light source) excite excess carriers in a first portion of the PV device, which induce a voltage in the PV device resulting in luminescence in a second portion of the PV device. If the light is localized to a small region of the PV device, contacting and conducting structures such as the emitter and base, and the emitter contacts and grids allow the induced voltage to spread to the rest of the device. Thus, the portion of the PV device not illuminated is subjected to a voltage applied across the junction of the device, and injects carriers, resulting in the creation of luminescence from the non-illuminated portion of the PV device. So, to collect a luminescence image for the PV device of interest, a localized area may be illuminated while a non-illuminated, substantially non-overlapping area of the device is imaged. Subsequently, the light source may be redirected to a different substantially non-overlapping area such that the previously illuminated region may also be imaged by detecting the luminescence it produces as a result of the redirected light source illuminating the different, substantially non-overlapping area. Thus, the illuminating/luminescing step may be repeated as needed to evaluate the light-collecting surface of the PV device being evaluated. For example, if 100% of a light collecting surface is to be imaged and evaluated for defects, a minimum of two images needs to be acquired to create a composite image of the entire surface. However, large PV modules and/or PV panels may require more that two successive illuminating/luminescing steps to evaluate 100% of the light-collecting surfaces.

Figure 2A:
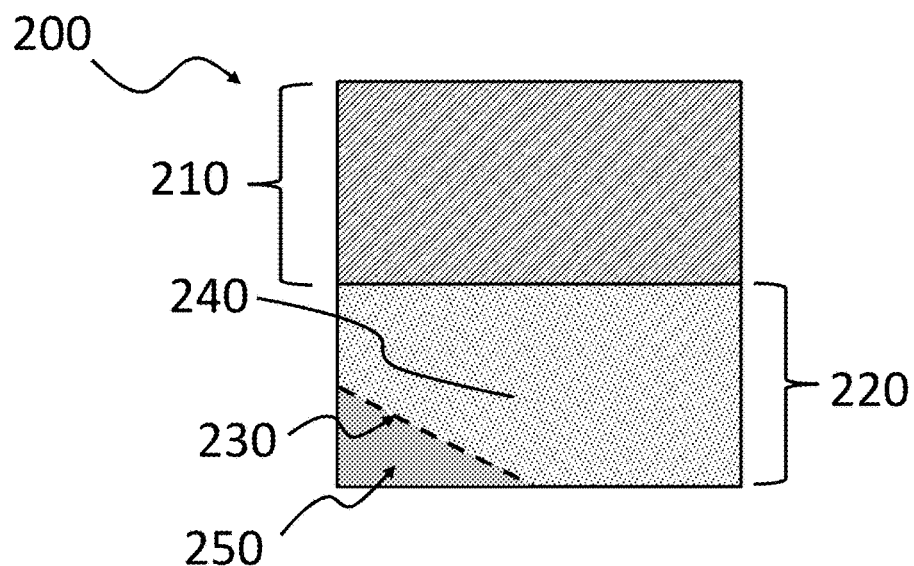
FIGS. 2a-c illustrate a two-step method for detecting defects in a PV device, according to exemplary embodiments of the present invention.
Figure 2B:
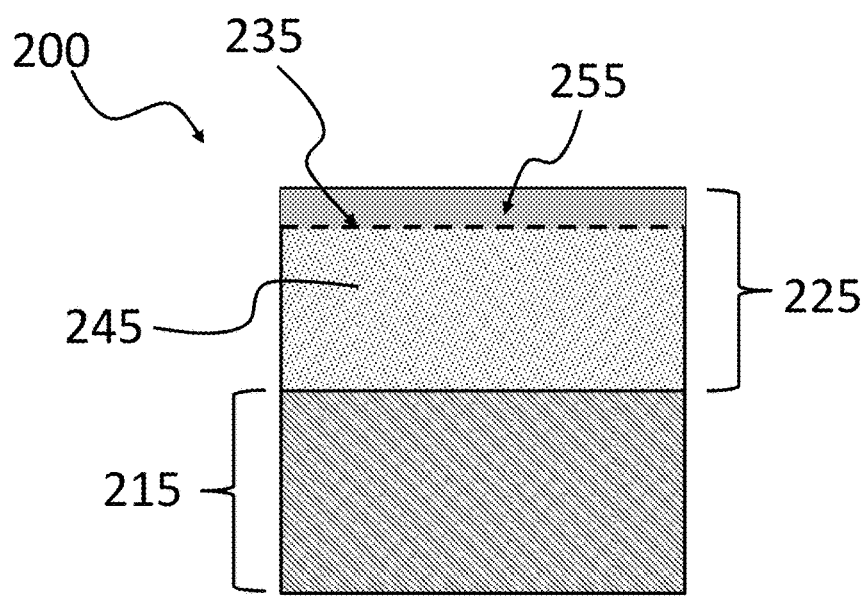
Figure 2C:
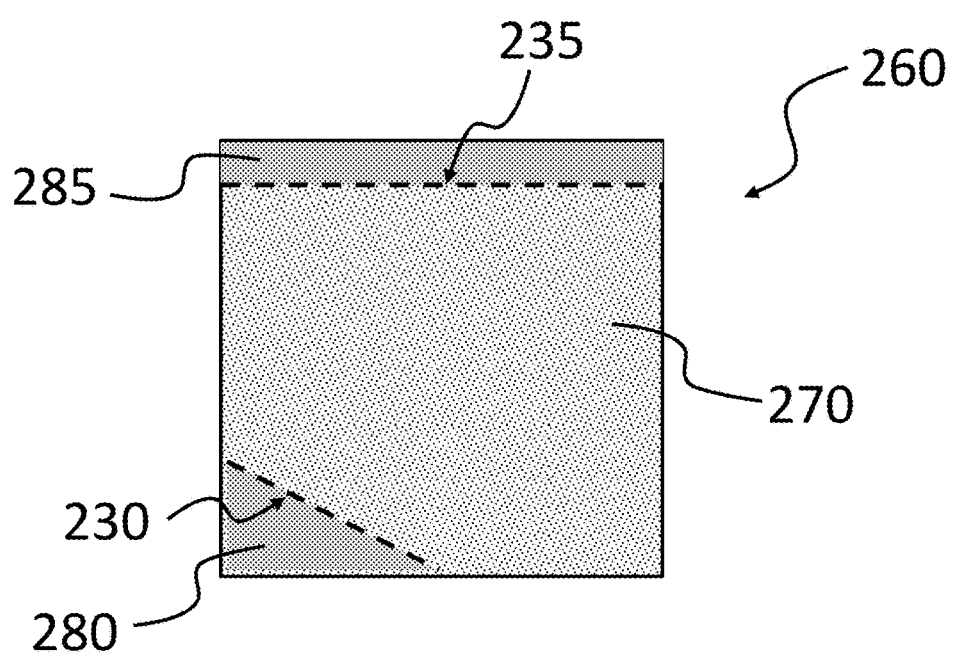

FIGS. 2a-c illustrate an embodiment of the present invention for detecting defects within a single PV device 200, that completes an analysis of 100% of the light-collecting surface in two successive steps. FIGS. 2a and 2b show top views of the surface of a PV device 200 that is normally positioned to receive electromagnetic radiation (e.g. solar radiation or sunlight) for generating an electrical current and/or voltage. Referring to FIG. 2a, in a first step of this example, a first portion (e.g. the top half) of the light-receiving surface of the PV device 200 is illuminated to create an illuminated portion 210 of the light-receiving surface of the PV device 200. The illumination may be achieved using a light-source other than the sun (e.g. a non-solar source), such as a lamp as described above, or a lamp may be used in addition to solar radiation. The illumination causes the formation of a voltage within the illuminated portion 210 of the PV device 200, and this voltage induces luminescence in at least parts of the non-illuminated portion 220 (e.g. the bottom half) of the PV device 200. However, one or more defects, e.g. a single crack 230 as shown in FIG. 2a, may prevent a section of the non-illuminated portion 220 of the PV device 200 from luminescing, resulting in a non-luminescing portion 250 within the non-illuminated portion 220 of the PV device 200. A first image (e.g. a first photograph) may than be taken (e.g. using a camera) and saved of the luminescing portion 240 and non-luminescing portion 250 of the non-illuminated portion 220 of the PV device 200. Alternatively, a first image may be taken of the entire PV device 200, to be saved for later processing (e.g. cropping/removal of the illuminated portion 210).

Referring now to FIG. 2b, the illumination may then be applied in a second step to the portion of the PV device 200 that was not illuminated during the first step. Thus, a second portion (e.g. the bottom half) of the light-receiving surface of the PV device 200 may be illuminated to create an illuminated portion 215 of the light-receiving surface of the PV device 200. As in the first illuminating step, the second illuminating step may be achieved using a light-source other than the sun (e.g. a non-solar source), such as a lamp as described above, or a lamp may be used in addition to the solar radiation. The illumination causes the formation of a voltage within the illuminated portion 215 of the PV device 200, and this voltage induces luminescence in at least parts of the non-illuminated portion 225 (e.g. the top half) of the PV device 200. However, one or more defects, e.g. a single crack 235 as shown in FIG. 2b, may prevent a first portion of the non-illuminated portion 225 of the PV device 200 from luminescing to form a non-luminescing portion 255 within the non-illuminated portion 225 of the PV device 200. A second image (e.g. a second photograph) may than be taken (e.g. using a camera) and saved of the luminescing portion 245 and non-luminescing portion 255 of the non-illuminated portion 225 of the PV device 200. Alternatively, a first image may be taken of the entire device 200, to be saved for later processing (e.g. cropping/removal of the illuminated portion 210).

To complete the evaluation of the entire surface of the PV device 200, the two images (e.g. two photographs) of the two non-illuminated portions 220 and 225 of the PV device 200 collected separately from the two separate illuminating steps, may be combined to create a single composite image 260 of the entire light-receiving surface of the PV device. Such an image may clearly identify the defects (e.g. cracks 230 and 235), as well as potentially ineffective areas 280 and 285, which may not be capable of effectively converting solar radiation to electricity, as well as the percentage of the light-receiving surface area of the PV device 200, that is effective area 270 for converting solar radiation to electricity. In this fashion, two or more illuminating/luminescence steps may be completed in series to evaluate 100% of the PV device's surface, where the PV device is at least one of a PV cell, a PV module, a PV panel, and/or a PV array. The two or more images may be combined to create a single or multiple composite images of the entire PV device 200.

FIGS. 2a and 2b illustrate an embodiment where the illuminated portions 210 and 215 are adjacent to (e.g. neighboring) the non-illuminated portions 220 and 225 that are being evaluated for luminescence using a detector (e.g. a camera). However, it is not necessary that the non-illuminated portions evaluated for luminescence be adjacent to the illuminated portions 210 and 215 of the PV device 200. In some embodiments of the present invention, there may be a third, intervening portion of the PV device positioned between the illuminated portion and the non-illuminated portions of the PV device. In general, the methods described herein will function properly when the illuminated portion and the non-illuminated, luminescing portion being imaged are connected electrically (e.g. a conductive pathway such as metal) to allow the transfer of the voltage induced in an illuminated portion to a non-illuminated portion.

Figure 3A:
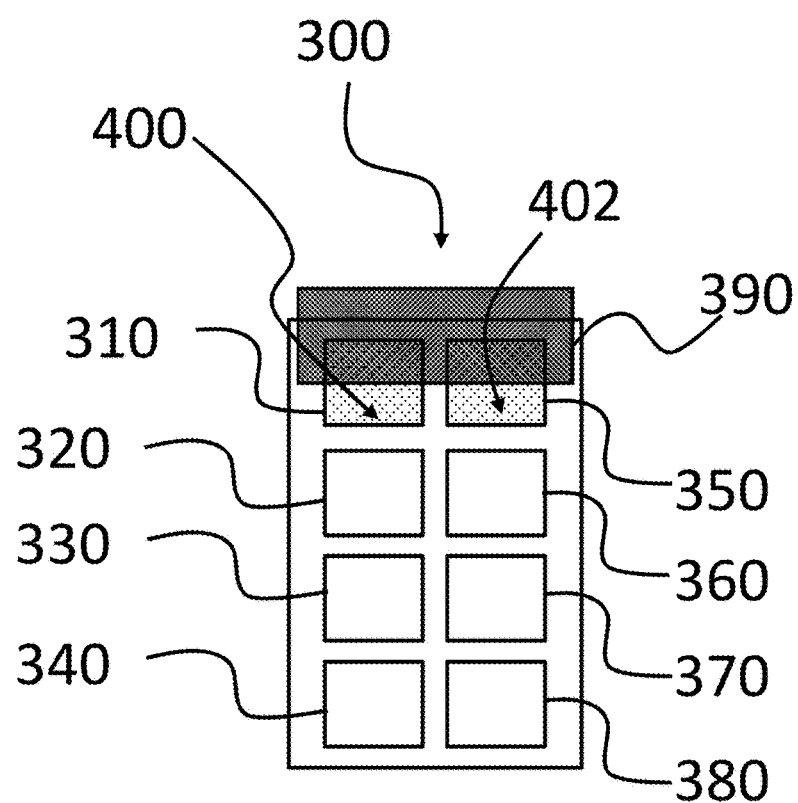
FIGS. 3a-c illustrate a method for detecting defects in a PV panel and/or PV module, according to exemplary embodiments of the present invention.
Figure 3B:
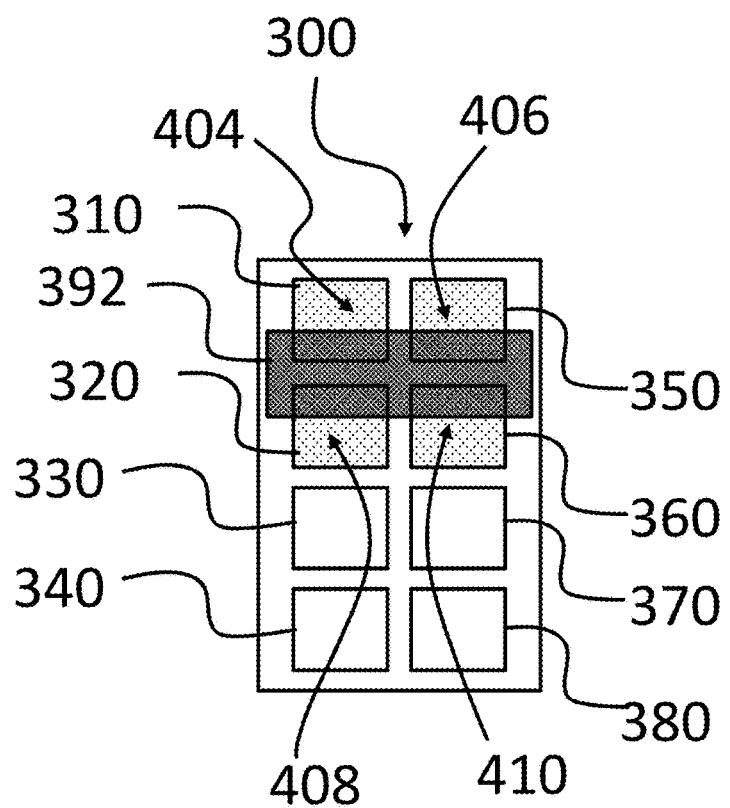
Figure 3C:
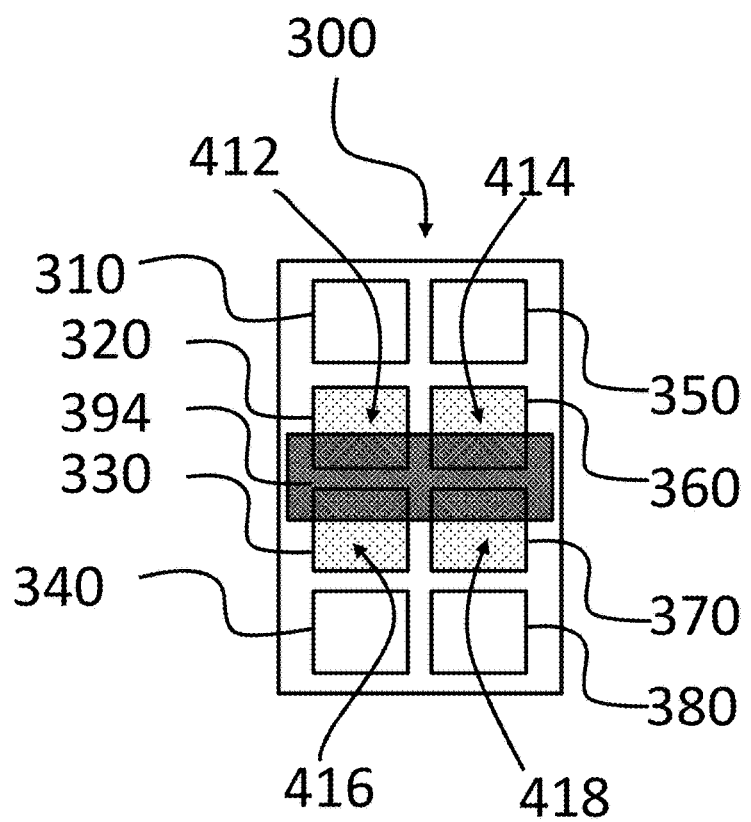

FIGS. 3a-c illustrate an example of a method for detecting defects within a PV module 300 constructed of eight separate PV cells (310, 320, 330, 340, 350, 360, 370, and 380). In this example, the method includes a series of illumination steps, with each illumination step illuminating a substantially different portion of the PV module 300, while simultaneously detecting and measuring the luminescence induced in other substantially different portions of the PV module (e.g. neighboring, non-illuminated portions). For example, a light source (not shown) is sequentially moved from a first location to one or more different locations, relative to the PV module 300. Alternatively, and/or in addition to, the light source may be redirected to different portions of the light-receiving surfaces of the PV module such that the light source remains substantially fixed in space and relative to the PV module. In this example, referring to FIG. 3a, the defect detecting method begins with a first illuminating step that positions the light source (not shown) to create a first illuminated portion 390 of a surface of PV module 300. During this first exemplary illumination step, the first illuminated portion 390 includes portions of the top two PV cells 310 and 350 of the PV module 300, causing the formation of voltages within each of these PV cells, and resulting in the formation of first luminescing portions 400 and 402 of the non-illuminated portions of the PV cells 310 and 350. Visualization of the first luminescing portions 400 and 402, as well as visualization of non-luminescing portions (not shown) within and/or bordering the first luminescing portions 400 and 402, enables the identification of defects, such as cracks, (not shown) within those first luminescing portions 400 and 402. During and/or at the conclusion of this first exemplary illuminating step, a first photograph may be taken of at least the first non-illuminated portions of PV cells 310 and 350.

This example continues with FIG. 3b, which illustrates a second illuminating step where the light source (not shown) is repositioned (and/or redirected) such that at least a part of the previously non-illuminated portions (e.g. the first luminescing portions 400 and 402 of the non-illuminated portions of the top two PV cells 310 and 350 from the first illuminating step) is now included in second illuminated portion 392 of the PV module 300. In addition, during this exemplary second illuminating step, the top portions of PV cells 320 and 360 (in the row of PV cells below PV cells 310 and 350) are included in second illuminated portion 392 of PV module 300. Thus, the newly positioned and/or redirected light source (not shown) creates second illuminated portion 392, which simultaneously includes portions of four PV cells (310, 320, 350, and 360), causing voltages to be formed in all four PV cells (310, 320, 350, and 360), resulting in the formation of multiple simultaneously luminescing portions (404, 406, 408, and 410) in the second non-illuminated portions of the PV cells (310, 320, 350, and 360). Visualization of the second luminescing portions (404, 406, 408, and 410), as well as visualization of non-luminescing portions (not shown) within and/or bordering the second luminescing portions (404, 406, 408, and 410), enables the identification of defects, such as cracks, (not shown) within the second luminescing portions (404, 406, 408, and 410) of the PV cells (310, 320, 350, and 360). During and/or at the conclusion of the second illuminating step, a second photograph may be taken of at least the second luminescing portions (404, 406, 408, and 410) within the non-illuminated portions of PV cells 310, 320, 350, and 360.

This example continues with FIG. 3c, which illustrates a third illuminating step where the light source (not shown)

may be repositioned (and/or redirected) such that at least a part of the previously non-illuminated portions (e.g. the luminescing portions 408 and 410 of the second row of PV cells 320 and 360 from the second illuminating step) are now included in a third illuminated portion 394 of the third illuminating step. In addition, during this exemplary third illuminating step, the top portions of PV cells 330 and 370 (in the row of PV cells below PV cells 320 and 360) are included in the third illuminated portion 394 of the PV module 300. Thus, the newly positioned light source (not shown) creates third illuminated portion 394, which simultaneously includes portions of four PV cells (320, 330, 360, and 370), causing voltages to be formed in all four PV cells (320, 330, 360, and 370), and resulting in the formation of multiple (third) simultaneously luminescing portions (412, 414, 416, and 418) in the third non-illuminated portions of the four illuminated PV cells (320, 330, 360, and 370). Visualization of the third luminescing portions (412, 414, 416, and 418), as well as visualization of non-luminescing portions (not shown) within and/or bordering the third luminescing portions (412, 414, 416, and 418), enables the identification of defects, such as cracks, (not shown) within those luminescing portions (412, 414, 416, and 418). During and/or at the conclusion of this third exemplary illuminating step, a third photograph may be taken of at least the non-illuminated portions of the PV cells (320, 330, 360, and 370) and the luminescing portions (412, 414, 416, and 418) contained therein.

By repeating these steps, all of the PV cells (310 through 380) and their respective light-receiving areas may be evaluated for defects. For example, referring again to FIGS. 3a-c, if the same general surface area and shape used for the first three illuminated portions (390, 392, and 394) is utilized in additional illuminating steps, about two more illuminating steps (a fourth and a fifth) would be required to complete an evaluation of 100% of the PV cells and their associated surface areas. Thus, by moving the light source (not shown), 100% of the PV cells and their corresponding surface areas could be illuminated, resulting in a corresponding luminescence (if possible) of all of the PV cells and their associated surface areas. In addition, after completion of the minimum number of illuminating steps (e.g. about 5 for this example), the images of the PV module 300 resulting from the multiple illuminating/luminescing steps may be spliced together to generate one or more composite images (not shown) of the entire PV module 300. The composite images may then be used to quantify the condition of the PV module 300, for example the percentage of surface area of the PV module 300 that is undamaged and/or capable of efficient conversion of solar radiation to electricity and/or the percentage of surface area of the PV module 300 that is potentially damaged and/or incapable of efficient conversion of solar radiation to electricity. In addition, the illuminating/luminescing steps may be repeated as needed on each PV module and/or each PV panel of a PV array until an entire PV array has been evaluated for defects that may negatively impact the PV array's ability to generate power, e.g. by generating visual images such as gray-scale images or data files that may be processed by a computer processer to identify these defects and quantify the PV array's potential performance metrics. Images may be cropped and stitched together using image processing software, such as ImageJ, Adobe Photoshop, Mathworks Matlab, or Wavemetrics Igor.

Referring again to the example method illustrated in FIGS. 3a-c, the illuminated portions (390, 392, and 394) may cover up to 50% of the light-receiving surface areas of four neighboring PV cells (e.g. see FIG. 3b and PV cells 310, 320, 350 and 360) within a PV module 300, while the luminescing portions of the non-illuminated portions are measured and/or photographed (e.g. see FIG. 3b and luminescing portions 404, 406, 408, and 410). The light source (not shown) may be moved to illuminate neighboring PV cells having adjacent corners, while the non-illuminated portions of the PV cell are measured and/or photographed for luminescence. Hardware may move the light source, such as translation and/or pointing, and the detector (e.g. camera) may also translate and combine images together as they are collected to form a composite luminescence map. In some embodiments, hardware may simultaneously move both the light source and the detector. The detector may have a field of view of the entire PV module. In this case, areas of images having luminescence information may be retained for visualization, quantification, analysis, etc., while illuminated portions may be cropped out and later replaced with images having luminescence information for this specific portions of the PV module. An algorithm may scan the non-illuminated/luminescing portions of the PV module to collect luminescence information of all of the light-collecting area of the PV module and assemble a composite luminescence map of the entire light-collecting area of the PV module.

In general, a detector, e.g. a camera, will collect light intensity measurements/data from the surfaces evaluated by the detector. Intensity measurements may include measurements of light emitted from the surfaces of the PV devices. Emitted light includes luminescence due to photoluminescence and/or electroluminescence. The light intensity measurements/data may then be analyzed to generate one-dimensional and/or two-dimensional plots representing the PV device surfaces to enable visualization of the surfaces to detect potential defects in the PV devices.

The method for detecting defects within a PV device may be completed on a PV device having at least one PV cell. However, it should be understood that the methods described herein apply to any PV module with any number of PV cells. The number of PV cells utilized in a PV module and/or PV panel is often determined by the specific application, physical location and/or environment of the solar power system and can vary significantly from application to application. In addition, the methods and/or systems described herein may utilize one or more light sources for illuminating the PV device(s). For example, at least one light source may simultaneously illuminate at least a fraction of one PV cell, fractions of 2 PV cells, fractions of 3 PV cells, and/or fractions of 4 PV cells. In other cases, as many PV cells as is reasonable may be simultaneously illuminated and imaged, as defined by the light sources (one or more) and imaging limitations.

Illuminated portions are not limited to square or rectangular shapes. For example, the illuminated portion may be circular or oval in shape. Similarly, the first portion of an area illuminated by a light source may include a fractional area that is not equal to one half of the light-receiving surface of a PV device (e.g. PV cell, PV panel, and/or PV module). For example, the surface area of a PV device that is illuminated by one or more light sources may range from about 0.1% to about 95% of the light-receiving surface area of a PV device. Further, at least two images and/or photographs may be created to generate a composite image and/or photograph that enables visualization of the luminescing portions and non-luminescing portions of the PV device, the combination of which enable the detection of any defects present on the surface of the PV device. In general, at least two images are required to form a composite image of the PV cell. So, it is practical that approximately 50% of the PV cell is illuminated while the other 50% is imaged.

In some embodiments of the present invention, a single light source may be utilized and repositioned as needed to generate a composite map identifying the two-dimensional location of defects in a PV device. Alternatively, plurality of light sources may be used. For example, the illumination step may include many illuminated portions that either simultaneously illuminate about one half of every PV cell within a PV module and/or PV panel, or are quickly switched from PV cell to PV cell during the camera exposure time. The detector may have a field of view that encompasses the entire PV device and/or may view two or more fractions of the PV device, sequentially one at a time. The non-illuminated portions of the PV cells may be measured for luminescence. The at least one light source may illuminate the non-overlapping, non-imaged portion of the PV device in order to collect luminescence data for the remaining portions of the PV device. The images (minimum of two) may then be combined to form a composite luminescence image of the entire PV device (e.g. PV cell, PV panel, and/or PV module).

In some examples, a module line-scan measurement device and/or system may be utilized to illuminate and/or generate luminescence images of the PV device(s) being evaluated. For example, the light source may produce multiple illuminated portions and/or illuminated lines such that all PV cells within a row of a PV module may be illuminated (as shown in FIGS. 3a-c). A line-scan detector (camera) may then collect luminescence images of each PV cell within the row such that the field of view is a line behind and/or in front of an illumination line. A second set of light source(s) may continue to excite carriers in a row of PV cells as the leading edge of the light moves to the next row while the detector continues to image the current row. Alternatively, the light source may be quickly moved or aimed to accomplish the transition from one row to the next. The light source and camera may scan across a fixed PV module, or a PV module may be moved across a fixed detector field of view, such as on a conveyor belt in an assembly line. Light may be provided to each PV cell as the line scan detector collects the luminescence signal, with the light not illuminating the area being imaged by the detector.

In some embodiments of the present invention, the illuminating may be done without applying a modulating bias across the PV device, although the methods described herein may also be accomplished with a modulating bias connected to the PV device (e.g. a system having a modulating bias does not need to be disconnected from the modulating bias). The illumination may be accomplished using a monochromatic light source of any wavelength that may be absorbed by the PV device to be tested. The light source may also be a broadband (white) light source. In some embodiments of the present invention, the light source may provide a coherent light source, such as a laser and/or laser diode, or a non-coherent light source, such as a light-emitting diode (LED) light, incandescent light, halogen light, a fluoresecent light, a laser diode light, and/or any other suitable light. For situations where the PV device is a significant distance away from the light source, e.g. greater than 5 meters, a collimated light source such as a laser may be used. Combinations of these different light sources may also be used. For example, a light source may provide light with any single wavelength of less than about 1100 nm, or combination thereof. A light source may provide light with a wavelength ranging from about 400 nm to about 1200 nm.

The process of detecting luminescence and/or defects may be accomplished by a camera and/or any suitable detector. Examples of cameras that may be used in some embodiments of the present invention include Si cameras (CCD=charge-coupled device or CMOS=complimentary metal-oxide-semiconductor) and InGaAs (array=2 dimensional detector or line=1 dimensional detector) cameras. The methods describe herein for detecting defects in a PV device may be accomplished in the field (e.g. testing the PV panels of a power producing PV array and/or on a manufacturing floor), in residential settings, commercial settings, and/or in the laboratory. The methods described herein may also be used to detect defects in PV cells, and/or PV modules/PV panels anywhere along the manufacturing line and/or the supply chain. For example, these methods may be carried out on the manufacturing floor, after the device has been manufactured and assembled and prior to storage in the warehouse, before and after shipping to an intermediate or final installation site, before installation and/or after installation.

The luminescence imaging methods described herein may be performed at night with less background light, thus preventing disruption of the PV array's power production during the day. However, the luminescence imaging methods may also be utilized during the day by employing "lock-in data acquisition" methods to enhance the signal-to-noise ratio. The lock-in principle is useful for extracting signals from statistical noise. The primary signal should be capable of being periodically pulsed and/or modulated with a certain lock-in frequency. By averaging the signal at the relevant frequency and phase, the periodic signal is separated from the background noise where the small signal is embedded. In some embodiments of the present invention, utilizing lock-in acquisition, the illumination may be pulsed at a selected frequency, and camera frames may be processed using the selected frequency to extract the luminescence data. Detector collection time (frame integration time) will be dependent upon the PV quality, background conditions, and desired image quality. For daytime testing, some embodiments of the present invention may also include a shading device to minimize the background signal provided by the sun. Some examples of a shading device include a movable screen, tarp, or sheet that is placed between the sun and the PV device.

The light source may be a laser diode, an LED, or any other light source with wavelengths that excite carriers in the PV material to generate a voltage. Depending on the material being imaged, the signal may be collected from a single exposure, or a lock-in acquisition method may be used to enhance the signal. In the case of lock-in acquisition, the excitation light may be modulated at an appropriate frequency for the camera frame rate and integration time. The cameras used in the examples illustrated in FIGS. 4a-b (and FIGS. 5a-b below) included a Princeton Instruments PIXIS 1024BR Si charge-coupled-device camera and a FLIR SC2500N InGaAs camera with lock-in data acquisition. When the lock-in process is used, the camera is triggered with a signal that is the same frequency as the excitation applied to the sample to be measured, and the excitation may be, for example, an applied voltage or light. The camera images are processed based on the lock-in frequency. The signal-to-noise ratio of a lock-in system is improved because background noise at frequencies other than the lock-in frequency is suppressed.

In some embodiments of the present invention, it is envisioned that the luminescence methods for detecting defects in PV devices described herein may be completed with the PV device operating in open circuit mode, short circuit mode, or under a normal operational load. In some examples, the detecting step(s) may be accomplished with or without the use of a filter. The imaging techniques and methods described herein may be automated and/or employ remote acquisition using either land rovers, robotic PV array crawlers, or flying drones/helicopters.

Figure 4A:
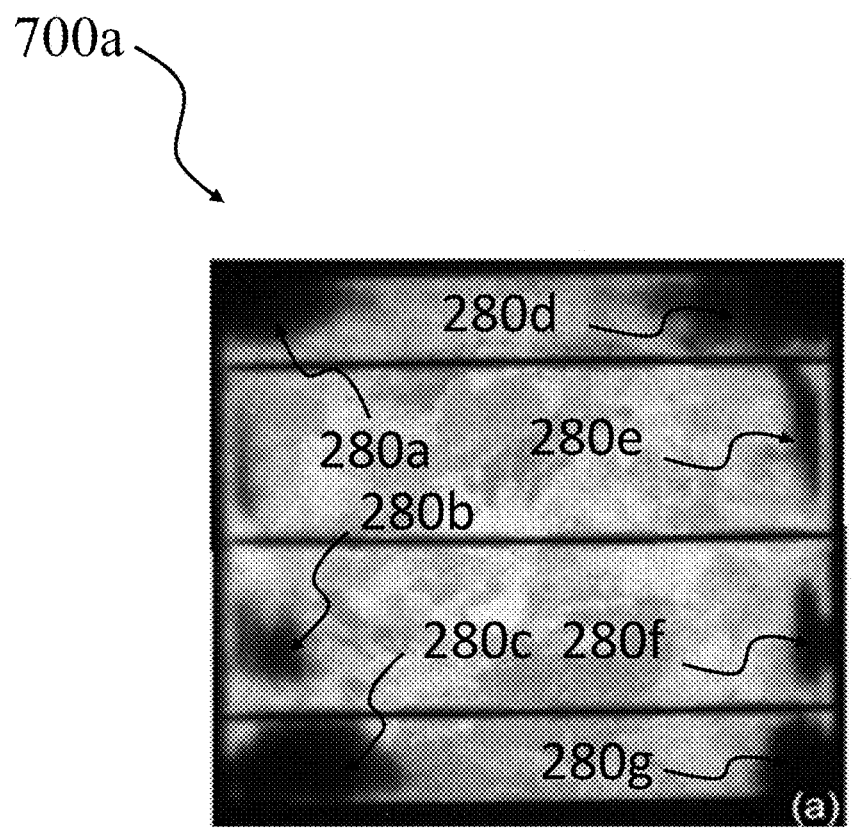
FIGS. 4a and 4b illustrate a comparison of defect detection methods of a multi-crystalline silicon PV cell: (a) an electroluminescing image where a voltage bias was applied to the PV cell in a dark enclosure, and (b) a luminescing image acquired by light-induced voltage where light was applied to opposite halves of the PV cell, and the two separate images corresponding to opposite halves of the PV cell were subsequently spliced together to form the complete image shown, according to exemplary embodiments of the present invention.
Figure 4B:
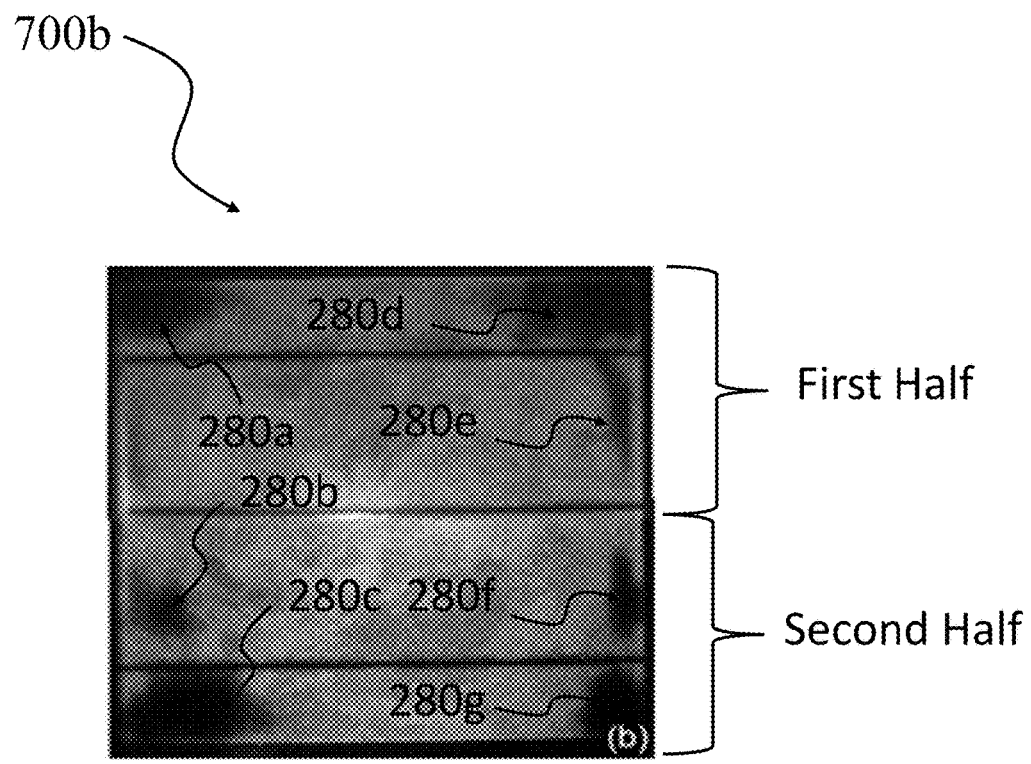

FIGS. 4a and 4b illustrate luminescence images 700a and 700b obtained of a multi-crystalline PV cell, utilizing two different methods. Both methods produce images 700a and 700b that identify at least seven non-luminescing portions, potentially ineffective areas 280a-g within the PV cell. These dark areas are identified as corrosion of the contacting metal grid components due to environmental stressing. However, the method used to obtain the image 700a illustrated in FIG. 4a required and used an applied biasing voltage to the entire PV cell (a connected power source) and is commonly referred to as electroluminescence. In contrast, the method used to obtain the image 700b illustrated in FIG. 4b was obtained without the application of any external voltage, power source and/or power system, according to some embodiments of the present invention. Referring to FIG. 4b, the luminescence shown in the first half of the PV cell was collected in a first illumination step, when a light source illuminated and excited carriers on the bottom half of the PV cell, in the absence of an externally provide power source. Similarly, the luminescence image for the second half of the PV cell was collected in a second, subsequent step while the top half of the PV cell was illuminated by a light source to excite carriers. The two luminescence images were then combined to form the complete composite luminescence image 700b shown in FIG. 4b. The electroluminescence image 700a illustrated in FIG. 4a was also collected in two halves, which were subsequently combined to provide a comparison with the same pixel resolution of the camera for both composite images.

In FIG. 4a, an LED emitting cool white light (~400 nm to ~1000 nm, 5000 K spectrum) illuminates approximately 40% of the PV cell with an intensity of ~1 Sun (~100 mW/cm$^2$). The ~80 Watt, ~140 Lumens/Watt LED is approximately 15 cm away from the PV cell, and the light spreads out over the illuminated portion of the PV cell within 20% uniformity. A Si CCD camera sensitive to near-IR wavelengths (~400 nm to ~1100 nm) collects the luminescence from 50% of the PV cell on the side that is not illuminated. Luminescence from silicon (the type of PV cell in FIGS. 4a and 4b) typically emits from ~1000 nm to ~1200 nm.

Figure 5A:
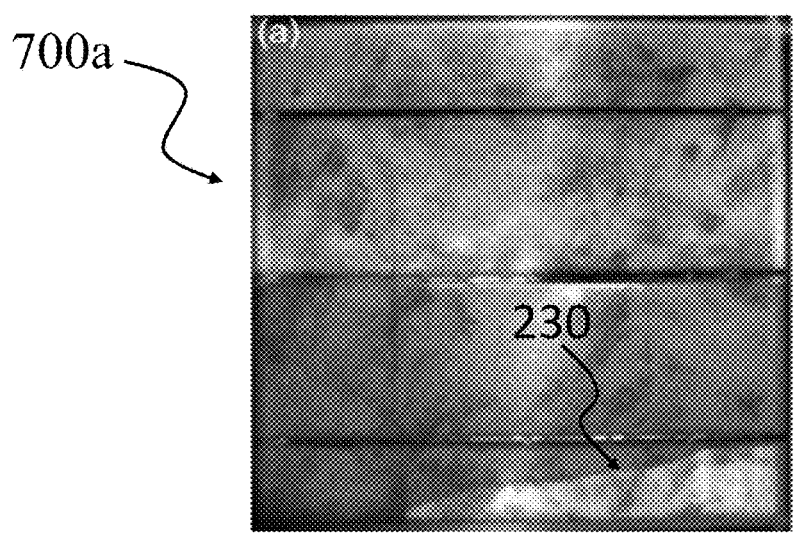
FIGS. 5a and 5b illustrate a comparison of defect detection methods of a multi-crystalline silicon PV cell: (a) an image of multi-crystalline silicon PV cell obtained by photoluminescence, and (b) a luminescing image of the same PV cell acquired by light-induced voltage, according to exemplary embodiments of the present invention. Both images where acquired in two steps where light was applied to opposite halves of the PV cell, and the two separate images corresponding to opposite halves of the PV cell were subsequently spliced together to form the complete images shown.
Figure 5B:
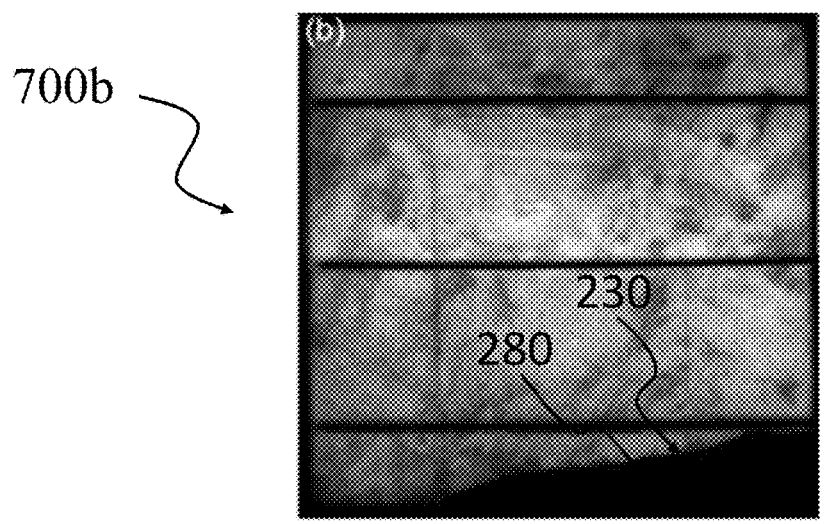

FIGS. 5a and 5b also illustrate luminescence images 700a and 700b obtained of a multi-crystalline PV cell, utilizing two different methods. Both methods produce images 700a and 700b that identify a crack 230 within the PV cell. However, only FIG. 5b illustrates the potentially deleterious consequences of the crack 230 by also identifying the non-luminescing portion 250 of the PV cell. In this example, one PV cell within a PV module containing 60 PV cells was imaged by a photoluminescence (PL) method and a non-photoluminescence method, both without electrical contact to the PV cell. The PL image 700a was collected using modulated excitation light that fully illuminated the entire PV cell. In this example, an optional filter on the camera blocked reflected excitation light while allowing the PL light to be imaged. This method identified the crack 230, however, was unable to identify the consequences of the crack 230, a portion of the PV cell that was electrically isolated from the rest of PV cell.

Contrary to this, the method used to generate the image 700b shown in FIG. 5b, according to some embodiments of the present invention, identified both the crack 230 and the resultant non-luminescing, potentially ineffective area 280 of the PV cell. The luminescence image illustrated in FIG. 5b was collected in two halves. The bottom half was imaged when light excited carriers on the top half, inducing a voltage on the bottom half. Due to a crack 230, the lower right region was isolated from the PV cell, and no voltage was present, leading to non-luminescing portion corresponding to potentially ineffective areas 280 of the PV cell. The top half can successfully be imaged as long as the illuminated portion on the bottom is large and not completely contained in a crack-isolated section of the PV cell. Also, unlike image 700a generated using PL, which required the use of a filter, the image 700b collected using the methods according to some embodiments of the present invention, did not use a filter.

The luminescence image of FIG. 5b illustrates how device performance-limiting defects can be detected and evaluated. The crack 230 and the non-luminescing portion, potentially ineffective area 280 are clearly visible in the lower right-hand corner. Also, differences in the gray-scale of the image clearly show differences in the PV cells behavior. Such gray-scale differences are even more visible in FIG. 4b. Thus, various imaging methods, such as gray-scale images, photos, videos, and other suitable 1D and 2D imaging methods may be utilized to visually detect defects, or alternatively, the images may be processed digitally by a computer processor to identify defects.

While the luminescence images here were collected for one PV cell, these methods can be scaled to test all the PV cells of a PV module, PV panel, and/or PV array. For example, the methods described herein may utilize a relatively large illuminated portion that excites carriers and induces voltage on four PV cells at a time by illuminating one corner of each PV cell simultaneously, where the four corners all meet at a point. Excitation light may be scanned to areas around the PV module, or multiple lights (and hence lighted areas) could be used in parallel, as the luminescence PV module image is collected. A line scan camera may also be used where areas of excitation light shine in front of and behind the imaged line as the system scans across the PV module.

Figure 6:
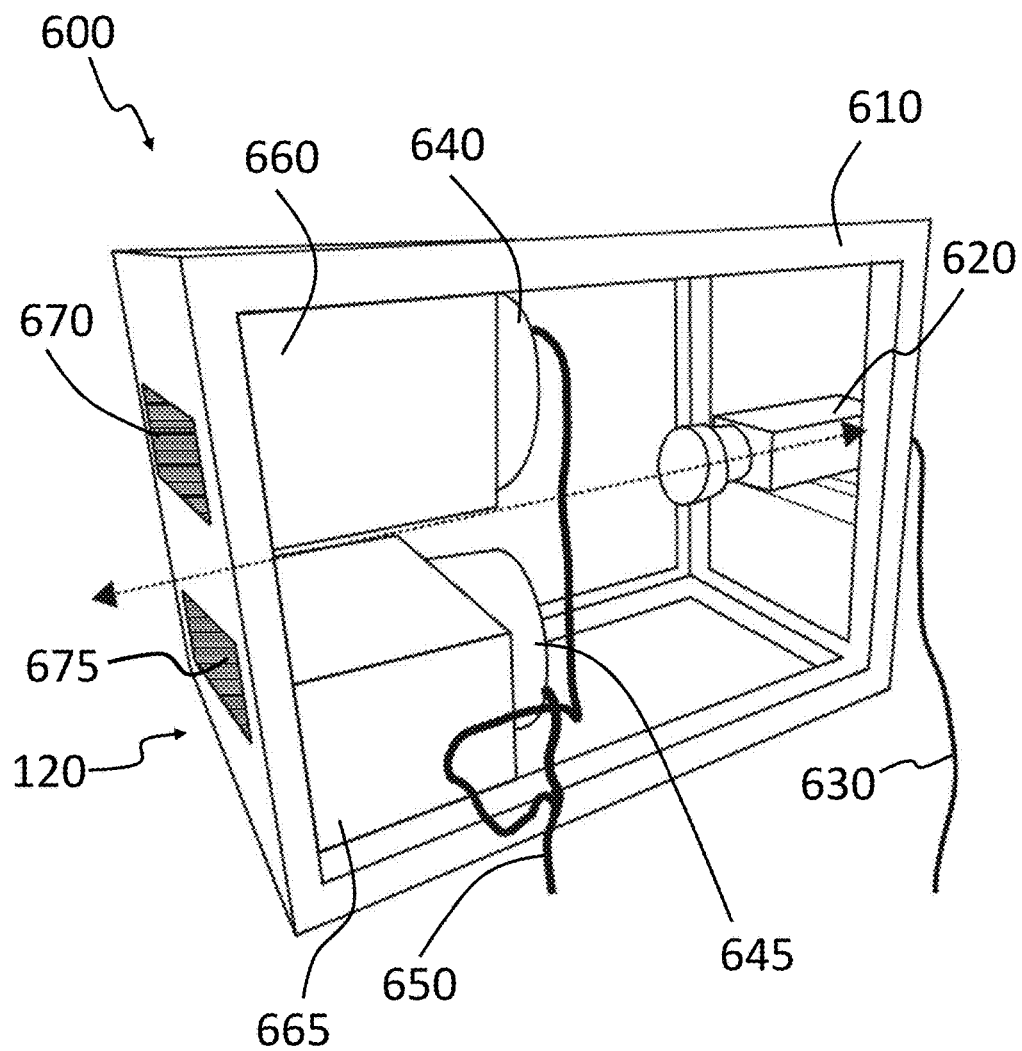
FIG. 6 illustrate a defect detection system for detecting defects in PV devices, according to exemplary embodiments of the present invention.

FIG. 6 illustrates a detection system 600 configured to detect defects in PV devices; e.g. PV cells, PV modules, and/or PV panels. The detection system 600 includes a support frame 610 that provides a physical structure for attaching and aligning the other components of the detection system 600, such as a camera 620, first light source 640, and a second light source 645. In this example, both light sources 640 and 645 are positioned within a first housing 660 and a second housing 665, respectively. In addition, each housing 660 and 665 has a corresponding aperture 670 and 675, respectively. Thus, as shown in FIG. 6, a technician may position the detection system 600 so that the apertures 670 and 675 are directed towards the light-collecting surfaces of a PV panel 120. The detection system 600 may be positioned directly in contact with the PV panel 120, thus automatically aligning the apertures 670 and 690 with the PV panel 120 such that the light illuminating the PV panel 120 strikes the PV panel 120 at an angle substantially perpendicular to the surface of the PV panel 120 and substantially parallel to the reference axis (dotted arrowed line) shown in FIG. 6. Similarly, placing the support frame 610 in direct contact with the PV panel 120 also aligns the camera 620 so that its orientation is substantially parallel to the PV panel 120.

However, placing the detection system 600 in direct contact with the PV panel 120 is not necessary, and it is envisioned that some embodiments of the present invention may evaluate PV devices by positioning detection systems at a specified distance from the PV devices being evaluated.

FIG. 6 illustrates the reference axis (dotted arrowed line) that indicates the longitudinal axis of the detection system 600, where the reference axis is substantially perpendicular to the light-collecting surface of the PV panel 120. The first light source 640 and the second light source 645 are positioned such that the light they produce is directed in an axis substantially parallel to the reference axis such that the light impinges the light-collecting surface of the PV panel 120 perpendicularly. The first aperture 670 of the first housing 660 containing the first light source 640 is positioned within a plane substantially perpendicular to the reference axis. Thus, the front face of the first housing 660 describes a plane containing the first aperture 670 such that placement of the support frame 610 against the light-collecting surface of the PV panel 120, automatically orients the front face of the first housing 660, and the first aperture 670, so that they are substantially parallel to the light-collecting surface of the PV panel 120, and the light from the first light source 640 strikes the PV panel 120 substantially perpendicular to its light-collecting surface. Similarly, the second aperture 675 of the second housing 665 containing the second light source 645 is positioned within a plane substantially perpendicular to the reference axis. Thus, the front face of the second housing 665 describes a plane containing the second aperture 675 such that placement of the support frame 610 against the light-collecting surface of the PV panel 120, automatically orients the front face of the second housing 665, and the second aperture 675, so that they are substantially parallel to the light-collecting surface of the PV panel 120, and the light from the second light source 645 strikes the PV panel 120 substantially perpendicular to its light-collecting surface.

Referring again to FIG. 6, two LEDs emitting cool white light (~400 nm to ~1000 nm, 5000 K spectrum) each illuminate approximately 40% of a typical 156-mm Si PV cell with an intensity of ~1 Sun (~100 mW/cm$^2$). Each ~80 Watt, ~140 Lumens/Watt LED is approximately 15 cm away from the PV module, and the light spreads out over the illuminated portion of the PV cells within 20% uniformity. The frame shown is 25 cm wide and 48 cm tall. The frame is 35 cm long, which is where the center of the camera is mounted. An InGaAs camera sensitive to near-IR wavelengths (~900 nm to ~1600 nm) collects the luminescence from the area of the PV cells (~75 mm height and ~150 mm width) that is between the illumination sources. Luminescence from silicon and CIGS typically emits in the ~1000 nm to ~1200 nm range. FIG. 6 also illustrates a data cable 630 for transferring image data to a computer system, and power cables 650 for the light sources 640 and 645.

Figure 7A:
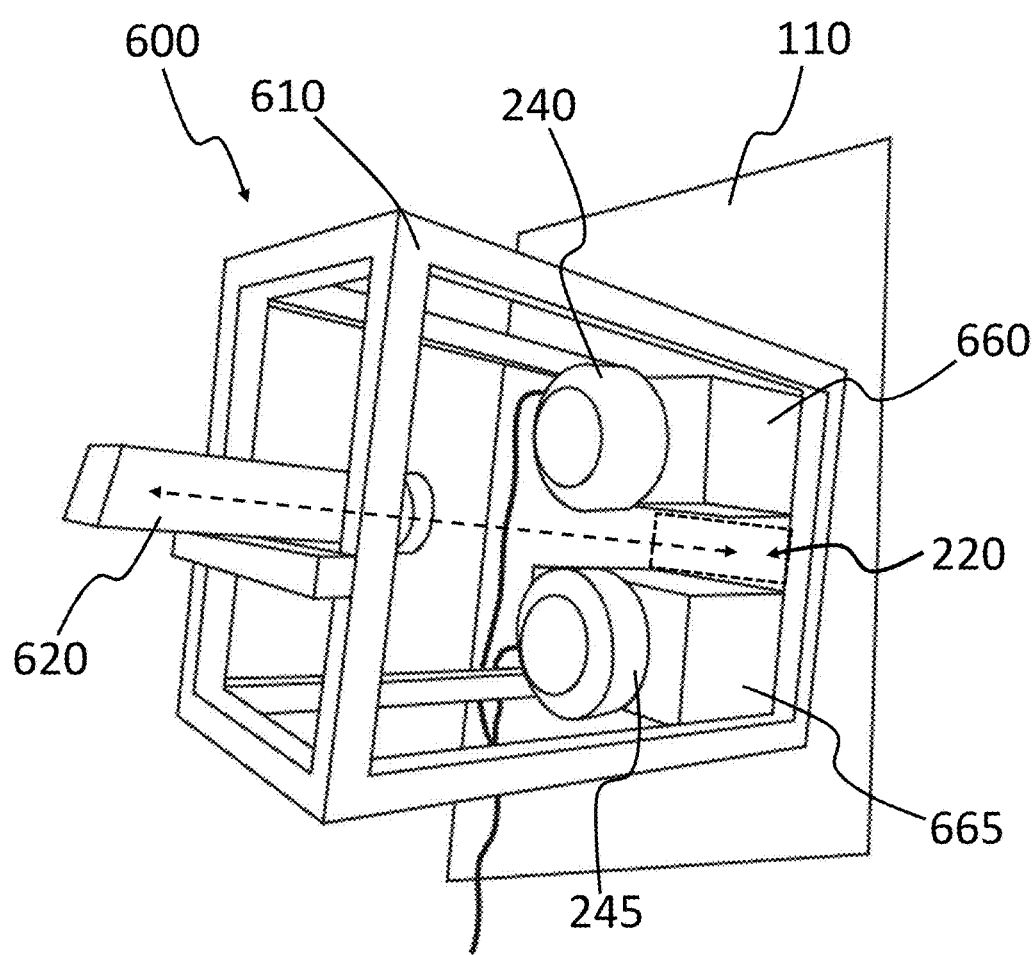
FIGS. 7a and 7b illustrate a defect detection system for detecting defects in PV devices and an exemplary luminescence image obtained for a multi-crystalline silicon PV panel using the defect detection system, according to exemplary embodiments of the present invention.

FIG. 7a illustrates the detection system 600 described above and illustrated in FIG. 6, in use to evaluate the condition of a multi-crystalline silicon PV module 110, although other PV devices could be evaluated in a similar manner. A technician has placed the front face of the support frame 610 of the detection system 600 in direct contact with the light-collecting surface of the multi-crystalline silicon PV module 110. The positioning of the detection system 600 in this manner has the effect of aligning the first light source 640 and the second light source 645 such that the light is directed onto the light-collecting surfaces of the PV module 110 at a substantially perpendicular angle and substantially parallel to the reference axis shown in FIG. 7a. Similarly, the positioning of the detection system 600 in this manner also aligns the camera 620 at an angle substantially perpendicular to the light-collecting surfaces of the PV module 110, and substantially parallel to the reference axis. FIG. 7a illustrates that the first housing 660 and the second housing 665 are spaced apart in a plane substantially perpendicular to the reference axis, forming a gap between the two housings 660 and 665. The camera 620 is positioned so that its field of view is focused on the non-illuminated portion 220 of the light-collecting surface of the PV module 110 that is visible between the gap. This portion of the PV module is a non-illuminated portion 220 that neighbors the portions of the light-collecting surfaces of the PV module that are directly illuminated by the light sources 640 and 645.

Figure 7B:
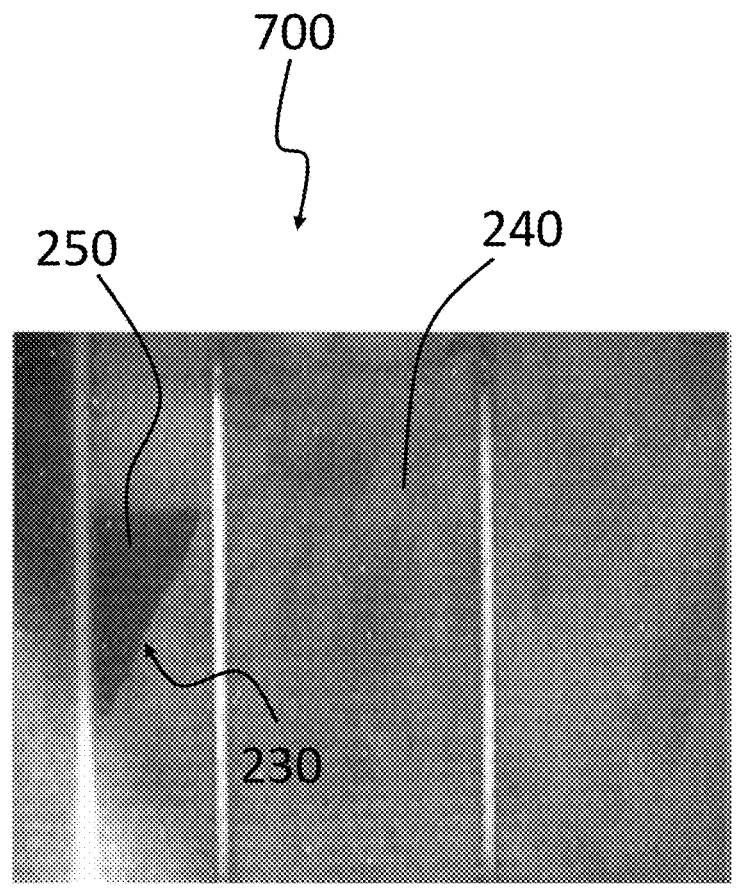

Thus, light provided by the light sources 640 and 645 to the illuminated portions of the multi-crystalline PV module (these illuminated portions not being visible in FIG. 7a since they are behind the housings 660 and 665) results in the production of excess carriers in the illuminated portions of the light-collecting surfaces of the PV module 110, which induce a voltage in the PV module 110, resulting in luminescence in the non-illuminated portion 220 of the PV module 110. The camera 620 then captures the luminescence to create an image 700 of non-illuminated portion 220 of the PV module 110. An exemplary image 700 of the non-illuminated portion 220 is illustrated in FIG. 7b. The image 700 clearly identifies luminescing portions 240 of the multi-crystalline PV module 110, as well as a non-luminescing portion 250, apparently created by a defect 230 (e.g. a crack).

Figure 8A:
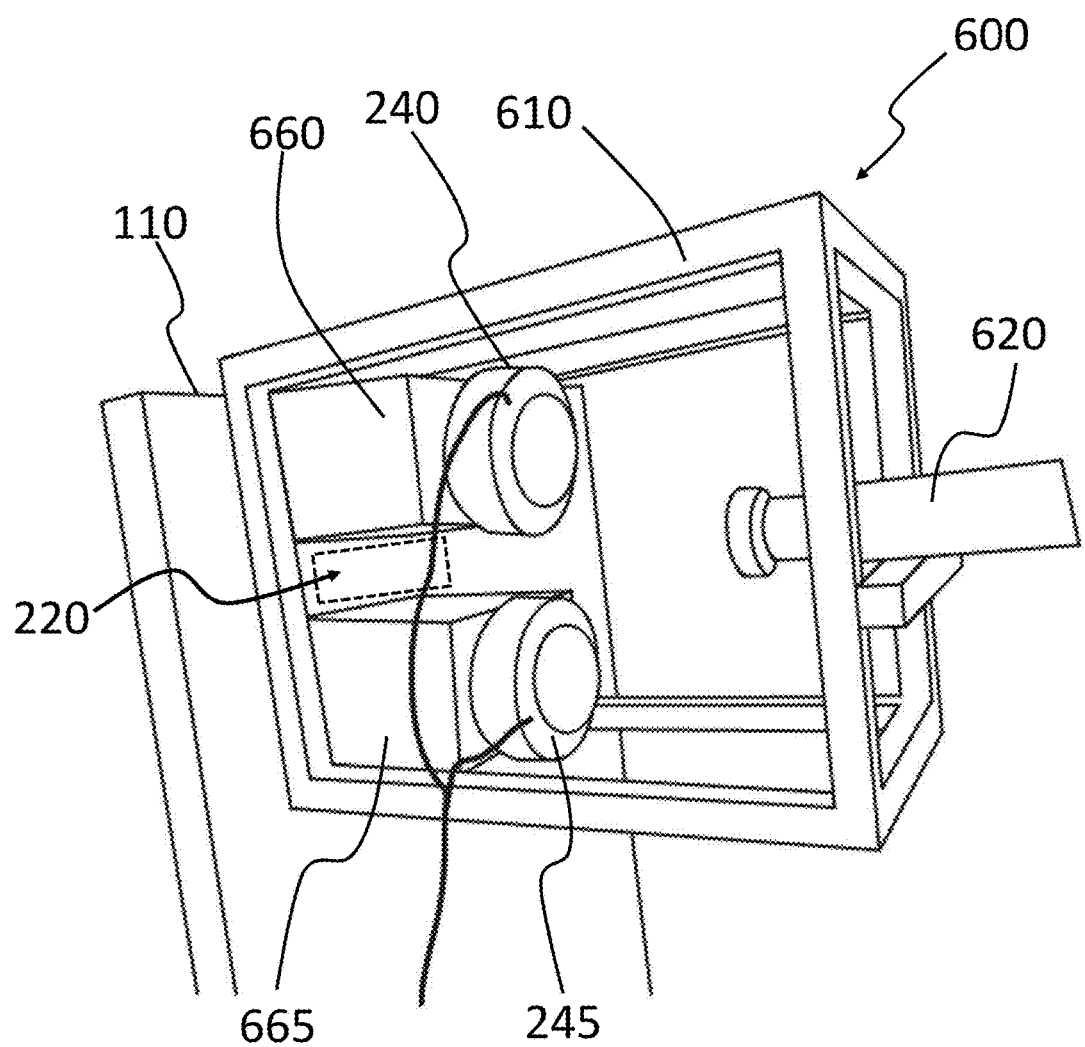
FIGS. 8a and 8b illustrate a defect detection system for detecting defects in PV devices and an exemplary luminescence image obtained for a CIGS PV panel using the defect detection system, according to exemplary embodiments of the present invention.

FIG. 8a illustrates the detection system 600 described above and illustrated in FIG. 6, in use to evaluate the condition of a copper, indium, gallium, selenide (CIGS) PV module 110. A technician has placed the front face of the support frame 610 of the detection system 600 in direct contact with the light-collecting surface of the CIGS PV module 110. The positioning of the detection system 600 in this manner has the effect of aligning the first light source 640 and the second light source 645 such that the light is directed onto the light-collecting surfaces of the PV module 110 at a substantially perpendicular angle and substantially parallel to the reference axis shown in FIG. 7a. Similarly, the positioning of the detection system 600 in this manner also aligns the camera 620 at an angle substantially perpendicular to the light-collecting surfaces of the PV module 110, and substantially parallel to the reference axis. FIG. 8a illustrates that the first housing 660 and the second housing 665 are spaced apart in a plane substantially perpendicular to the reference axis, forming a gap between the two housings 660 and 665. The camera 620 is positioned so that its field of view is focused on the non-illuminated portion 220 of the light-collecting surface of the CIGS PV module 110 that is visible between the gap. This portion of the PV module is a non-illuminated portion 220 that neighbors the portions of the light-collecting surfaces of the CIGS PV module that are directly illuminated by the light sources 640 and 645.

Figure 8B:
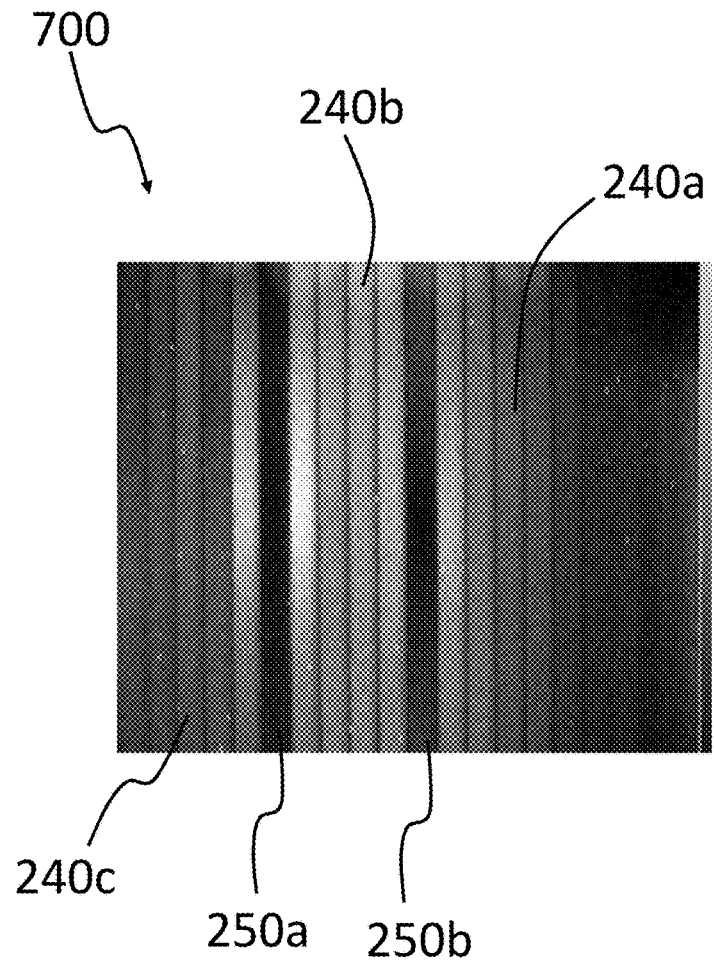

Thus, light provided by the light sources 640 and 645 to the illuminated portions of the CIGS PV module (these illuminated portions not being visible in FIG. 8a since they are behind the housings 660 and 665) results in the production of excess carriers in the illuminated portions of the light-collecting surfaces of the PV module 110, which induce a voltage in the PV module 110, resulting in luminescence in the non-illuminated portion 220 of the PV module 110. The camera 620 then captures the luminescence to create an image 700 of the luminescing, non-illuminated portion 220 of the CIGS PV module 110. An exemplary image 700 of the luminescing, non-illuminated portion 220 is illustrated in FIG. 8b. The image 700 clearly identifies luminescing portions 240a-c of the CIGS PV module 110, as well as a non-luminescing portions 250a and 250b, apparently created by defects outside of the field of view, apparently causing open circuits that prevent the transfer of the excess carriers into those portions of CIGS PV module 110.

PV module reliability is an important component to costs associated with solar power systems. The techniques, methods, devices, and systems presented herein provide the capability to identify defects within a PV device and how defects accumulate over time. Defect accumulation rates can then be correlated to performance and can thus lead to confidence for investors that PV performance can be tracked, both easily and frequently. The methods and systems described herein also provide simple, cost-effective, and reliable methods and systems for PV array plant operators to monitor the performance of their plants, thus providing an invaluable tool to assist with plant maintenance, thus increasing the power output of the PV array and decreasing the cost of each kilowatt produced. Imaging data can be used to ensure that transportation didn't cause damage that is not easily visible, such as cracked PV cells within the PV module. Imaging can also be used after installation to inspect for damage incurred during installation. Periodic imaging can supplement field performance data to identify PV module degradation and provide more detailed information on any patterns in degradation or defect propagation.

As used herein, the terms "substantially" and "about" refer to variation around a specified value (e.g. angle, distance, wavelength, etc.) of plus or minus 5% of the specified value.

The invention has been described with reference to various specific and preferred embodiments and techniques. However, it should be understood that many variations and modifications may be made while remaining within the spirit and scope of the invention. It is appreciated that certain features of the invention, which are, for clarity, described in the context of separate embodiments, may also be provided in combination in a single embodiment. Conversely, various features of the invention that are, for brevity, described in the context of a single embodiment, may also be provided separately or in any sub-combination.

The examples included above are included merely for the purposes of illustration of certain aspects of the embodiments of the present invention. The examples are not intended to limit the invention, as one of skill in the art would recognize from the above teachings and examples that other techniques and methods can satisfy the claims and can be employed without departing from the scope of the claimed invention

What is claimed is:

1. A method comprising:
    illuminating, using a non-solar light source, a first portion of a surface of a photovoltaic (PV) device;
    collecting, using a detector, a first set of measurements relating to at least one of the presence or absence of luminescence from a second portion of the surface that is not illuminated by the non-solar light source; and
    analyzing the first set of measurements to produce a first representation of the surface, wherein:
    the first representation identifies at least one of a first luminescing region or a first non-luminescing region within the second portion of the surface, and
    the first portion of the surface and the second portion of the surface are electrically connected.

2. The method of claim 1, wherein the illuminating and collecting are completed without attaching an external power source to the PV device and without detaching the PV device from a power component used during normal operation of the PV device.

3. The method of claim 1, further comprising:
    stopping the illuminating of the first portion of the surface by the non-solar light source;
    subsequently illuminating, using the non-solar light source, the second portion of the surface;
    collecting, using a detector, a second set of measurements relating to at least one of the presence or absence of luminescence from the first portion of the surface that is not illuminated by the non-solar light source;
    analyzing the second set of measurements to produce a second representation of the surface, wherein the second representation identifies at least one of a second luminescing region or a second non-luminescing region within the first portion of the surface; and
    combining the first representation with the second representation to produce a composite representation of the surface that includes both the first portion and the second portion of the surface.

4. The method of claim 3, wherein the non-solar light source and the detector are moved as a unit.

5. The method of claim 3, wherein the detector is moved independently of the non-solar light source.

6. The method of claim 1, wherein the illuminating and the collecting are performed while the surface of the PV device is further illuminated using a solar light source.

7. The method of claim 6, wherein the illuminating using the non-solar light source comprises at least one of pulsing or modulating the non-solar light source.

8. The method of claim 6, wherein the first set of measurements and the second set of measurements comprise luminescence intensity data from the second portion and the first portion of the surface, respectively.

9. The method of claim 1, wherein the non-solar light source provides light comprising at least one wavelength of less than about 1100 nm.

10. The method of claim 9, wherein:
    the first set of measurements and the second set of measurements comprise luminescence intensity data from the second portion and the first portion of the surface, respectively, and
    the luminescence intensity data are for light emitted with wavelengths greater than the at least one wavelength of the light provided by the non-solar light source.

11. The method of claim 1, wherein the non-solar light source comprises at least one of an light-emitting diode (LED) light, an incandescent light, a fluorescent light, a laser diode light, or a halogen light.

12. The method of claim 1, wherein the detector comprises at least one of a silicon camera or an indium-gallium-arsenide camera.

13. The method of claim 1, wherein the camera comprises at least one of a charge-coupled camera or a complimentary metal-oxide-semiconductor camera.

14. The method of claim 1, wherein the illuminating and the collecting are performed with both the non-solar light source and the detector within a distance of about six meters or less from the PV device.

15. The method of claim 1, wherein the illuminating and the collecting are performed with both the non-solar light source and the detector at a distance greater than about six meters from the PV device.

16. A system comprising:
- a non-solar light source configured to produce non-solar light having at least one wavelength less than about 1100 nm; and
- a camera configured to detect emitted light having a wavelength greater than the at least one wavelength produced by the non-solar light source, wherein:
- the non-solar light source is configured to direct the non-solar light substantially towards a first target, and
- the camera is configured to receive the emitted light from a second target that is electrically connected to the first target.

17. The system of claim 16, wherein the non-solar light source comprises at least one of an light-emitting diode (LED) light, an incandescent light, a fluorescent light, a laser diode light, or a halogen light.

18. The system of claim 16, wherein the camera comprises at least one of a silicon camera or an indium-gallium-arsenide camera.

19. The system of claim 16, further comprising a housing, wherein:
- the non-solar light source is positioned within the housing,
- the housing comprises an aperture, and
- the non-solar light produced by the light source passes through the aperture.

20. The system of claim 19, further comprising a support frame, wherein the housing and the camera are physically connected to the support frame, such that the housing, the non-solar light source, and the camera move as a unit when the support frame is moved.

* * * * *